(12) United States Patent
Ser

(10) Patent No.: US 10,533,844 B2
(45) Date of Patent: Jan. 14, 2020

(54) THREE-DIMENSIONAL SHAPE MEASURING APPARATUS USING DIFFRACTION GRATING

(71) Applicant: KOH YOUNG TECHNOLOGY INC., Seoul (KR)

(72) Inventor: Jang Il Ser, Gyeonggi-do (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/526,538

(22) PCT Filed: Nov. 11, 2015

(86) PCT No.: PCT/KR2015/012109
§ 371 (c)(1),
(2) Date: May 12, 2017

(87) PCT Pub. No.: WO2016/076626
PCT Pub. Date: May 19, 2016

(65) Prior Publication Data
US 2018/0283852 A1 Oct. 4, 2018

(30) Foreign Application Priority Data

Nov. 13, 2014 (KR) .................. 10-2014-0157805

(51) Int. Cl.
*G01B 11/02* (2006.01)
*G01B 11/24* (2006.01)
(Continued)

(52) U.S. Cl.
CPC ...... *G01B 11/2441* (2013.01); *G01B 9/02021* (2013.01); *G01B 9/02025* (2013.01);
(Continued)

(58) Field of Classification Search
CPC ............ G01B 11/2441; G01B 9/02021; G01B 9/02025; G01B 2210/56; G01B 2290/20; G01N 21/956
(Continued)

(56) References Cited

U.S. PATENT DOCUMENTS 5,764,363 A 6/1998 Ooki et al.
7,551,293 B2 * 6/2009 Yelin .................. G01B 11/2441
356/456
(Continued)

FOREIGN PATENT DOCUMENTS

CN 104034279 9/2014
JP 09-145330 6/1997
(Continued)

OTHER PUBLICATIONS

Tom Dewitt et al., "3-d Microscope using diffraction grating"; SPIE, 1996, vol. 2599, pp. 228-239.
(Continued)

*Primary Examiner* — Tarifur R Chowdhury
*Assistant Examiner* — Jonathon Cook
(74) *Attorney, Agent, or Firm* — Kile Park Reed & Houtteman PLLC

(57) ABSTRACT

Disclosed is a three-dimensional shape measuring apparatus using a diffraction grating, comprising: a light splitter installed in a traveling direction of a light generated from a light source unit and configured to reflect a portion of the light along a first path and transmit a portion of the light along a second path; an image sensor unit configured to receive a light traveling along the first path and reflected from a measurement target having at least one hole, and measure the shape of the measurement target; and a diffraction grating disposed on at least one light path among a light path between the light source unit and the light splitter, a
(Continued)

light path between the measurement target and the light splitter, and a light path between the measurement target and the image sensor unit.

8 Claims, 4 Drawing Sheets

(51) Int. Cl.
  *G01B 9/02* (2006.01)
  *G01B 11/06* (2006.01)
  *G01N 21/956* (2006.01)
(52) U.S. Cl.
  CPC ...... *G01B 9/02044* (2013.01); *G01B 11/0608* (2013.01); *G01N 21/956* (2013.01); *G01B 2210/56* (2013.01); *G01B 2290/20* (2013.01)
(58) Field of Classification Search
  USPC .......................................................... 356/511
  See application file for complete search history.

(56) References Cited

U.S. PATENT DOCUMENTS

| | | | |
|---|---|---|---|
| 2005/0128488 A1 | 6/2005 | Yelin et al. | |
| 2011/0242487 A1 | 10/2011 | Yuasa et al. | |
| 2011/0279822 A1* | 11/2011 | Kannaka | G01B 11/06 356/503 |
| 2013/0206992 A1 | 8/2013 | Jin et al. | |
| 2015/0235911 A1* | 8/2015 | Asano | B05C 21/005 438/7 |
| 2015/0338205 A1* | 11/2015 | Zhang | G01D 5/38 356/487 |
| 2015/0362308 A1 | 12/2015 | Jia et al. | |

FOREIGN PATENT DOCUMENTS

| | | |
|---|---|---|
| JP | 2000-097622 | 4/2000 |
| JP | 2006-116028 | 5/2006 |
| KR | 10-1242470 | 3/2013 |
| KR | 10-2014-0004943 | 1/2014 |
| KR | 10-1407482 | 6/2014 |
| KR | 10-1414255 | 7/2014 |

OTHER PUBLICATIONS

Jang-Il Ser et al.; "Applicability of diffraction grating to parallax image array generation in integral imaging"; Applied OPtics, vol. 49, No. 13, May 1, 2010, pp. 2429-2433.
International Search Report for International Application No. PCT/KR2015/012109, dated Feb. 3, 2016.
Written Opinion for International Application No. PCT/KR2015/012109 with English translations, dated Feb. 3, 2016.
Chinese Office Action with English Translation for Chinese Application No. 201580059588 dated Dec. 20, 2018.
Chinese Office Action with English translation for Chinese Application No. 201580059588.0, dated Aug. 9, 2019.

\* cited by examiner

THREE-DIMENSIONAL SHAPE MEASURING APPARATUS USING DIFFRACTION GRATING

TECHNICAL FIELD

The present invention relates to a three-dimensional shape measuring apparatus and, more specifically, to a three-dimensional shape measuring apparatus using a laser.

BACKGROUND ART

Recently, research on ultra-small-sized large-capacity semiconductor memories has been actively progressing. According to such research, technologies for increasing storage capacity of semiconductor memory elements through a multichip package, in which multiple semiconductor chips are mounted in one semiconductor package, are being developed.

In order to electrically connect circuit patterns formed in such multiple semiconductor chips, via holes (TSV: through silicon via) vertically passing through a silicon wafer substrate are formed. Such via holes should be formed according to a predetermined standard. Otherwise, a malfunction of a semiconductor package may be caused. Therefore, it is necessary to inspect whether the depth and shape of such via holes have been formed normally.

A conventional scheme employs an FSI, WSI, or confocal scheme that requires using a coaxial light in order to measure the depth of a hole. However, in the case of the confocal scheme, a point where a light spatially converges by a lens is used and thus, there is a problem in that, when a narrow and long hole is measured, the light converging toward a focal point is blocked by the opening.

Further, the conventional scheme uses a single camera for the measurement. However, in the case of such a single camera scheme, it is difficult to measure/inspect an inclined surface because a small amount of light is reflected. In addition, in the case of using multiple cameras to observe a side surface of a hole, not only is it difficult to bring the cameras into focus at the same time but also a distortion may occur in an image. This is because the measurement target (which is not a flat wafer and requires simultaneous measurement of multiple holes instead of a single hole) is not perpendicular but is inclined with respect to the viewing angles of the cameras. Accordingly, a close site may be distorted to be larger while a distant site may be distorted to be smaller, and since image formation surfaces may be inclined, it is difficult to bring the cameras into focus over the entire FOV at the same time.

(Prior Art Document) Korean Patent No. 10-1407482, (Article) Applicability of diffraction grating to parallax image array generation in integral imaging: Jang-Il Ser, Jae-Young Jang, Sungdo Cha, and Seung-Ho Shin, Department of Physics, Kangwon National University, Chuncheon 200-701, South Korea.

SUMMARY

The present invention is to provide a three-dimensional shape measuring apparatus that can measure, accurately and at a high speed, the depth of a hole, the shape of the hole (inner wall), and a measurement target in which the hole is formed.

A three-dimensional shape measuring apparatus using a diffraction grating according to an embodiment of the present invention includes: a light splitter installed in a traveling direction of a light generated from a light source unit and configured to reflect a portion of the light along a first path and transmit a portion of the light along a second path; an image sensor unit configured to receive a light traveling along the first path and reflected from a measurement target having at least one hole, and measure the shape of the measurement target; and a diffraction grating disposed on at least one light path among a light path between the light source unit and the light splitter, a light path between the measurement target and the light splitter, and a light path between the measurement target and the image sensor unit.

Further, in the three-dimensional shape measuring apparatus using the diffraction grating, the diffraction grating may diffract a light incident on the diffraction grating so that lights received by the image sensor have different parallax information.

Further, in the three-dimensional shape measuring apparatus using the diffraction grating, the image sensor unit may include a plurality of image sensors configured to receive the lights having the different parallax information through a single imaging lens and generate a plurality of images according to the respectively different parallax information.

Further, in the three-dimensional shape measuring apparatus using the diffraction grating, the measurement target may be disposed to reflect the light reflected along the first path by a front surface on which the hole is formed or a rear surface.

Further, in the three-dimensional shape measuring apparatus using the diffraction grating, when the measurement target is disposed to reflect the light reflected along the first path by the rear surface, the image sensor unit may measure the shape of the measurement target by receiving the light reflected from the rear surface of the measurement target and a light reflected from a bottom surface of the hole positioned inward of the rear surface of the measurement target that interfere with each other.

Further, the three-dimensional shape measuring apparatus using the diffraction grating may further include a reference mirror disposed in a traveling direction of the light transmitted along the second path to form a reference light to interfere with the light reflected from the measurement target, wherein the image sensor unit may measure the shape of the measurement target by using an interference signal according to superposition of the light reflected from the measurement target and the reference light.

Further, in the three-dimensional shape measuring apparatus using the diffraction grating, the diffraction grating may have a form of at least one among a lens array form, a lenticular form, a prism array form, a wire grid form, a concavo-convex form, a right triangle array form, and an isosceles triangle array form.

Further, the three-dimensional shape measuring apparatus using the diffraction grating may measure a three-dimensional shape of a via hole of a substrate as the measurement target.

A three-dimensional shape measuring apparatus using a diffraction grating according to an embodiment of the present invention can acquire an image of a blind spot, which cannot be measured in a single observation angle such as a vertical surface of a hole or the like, to measure and inspect the blind spot, and can reduce a measurement error due to vibration while enhancing the speed of inspection.

Further, by using a diffraction grating, the three-dimensional shape measuring apparatus using the diffraction grating can obtain a multi-view image through a single camera without an image distortion of a three-dimensional measurement target and a focal problem.

Therefore, the three-dimensional shape measuring apparatus using the diffraction grating is suitable for measuring a very thin and deep via hole (e.g., a through silicon via) that has an opening diameter of several μm to several hundred μm and an aspect ratio (depth to opening diameter of hole) of about 10:1.

DETAILED DESCRIPTION

Figure 1:
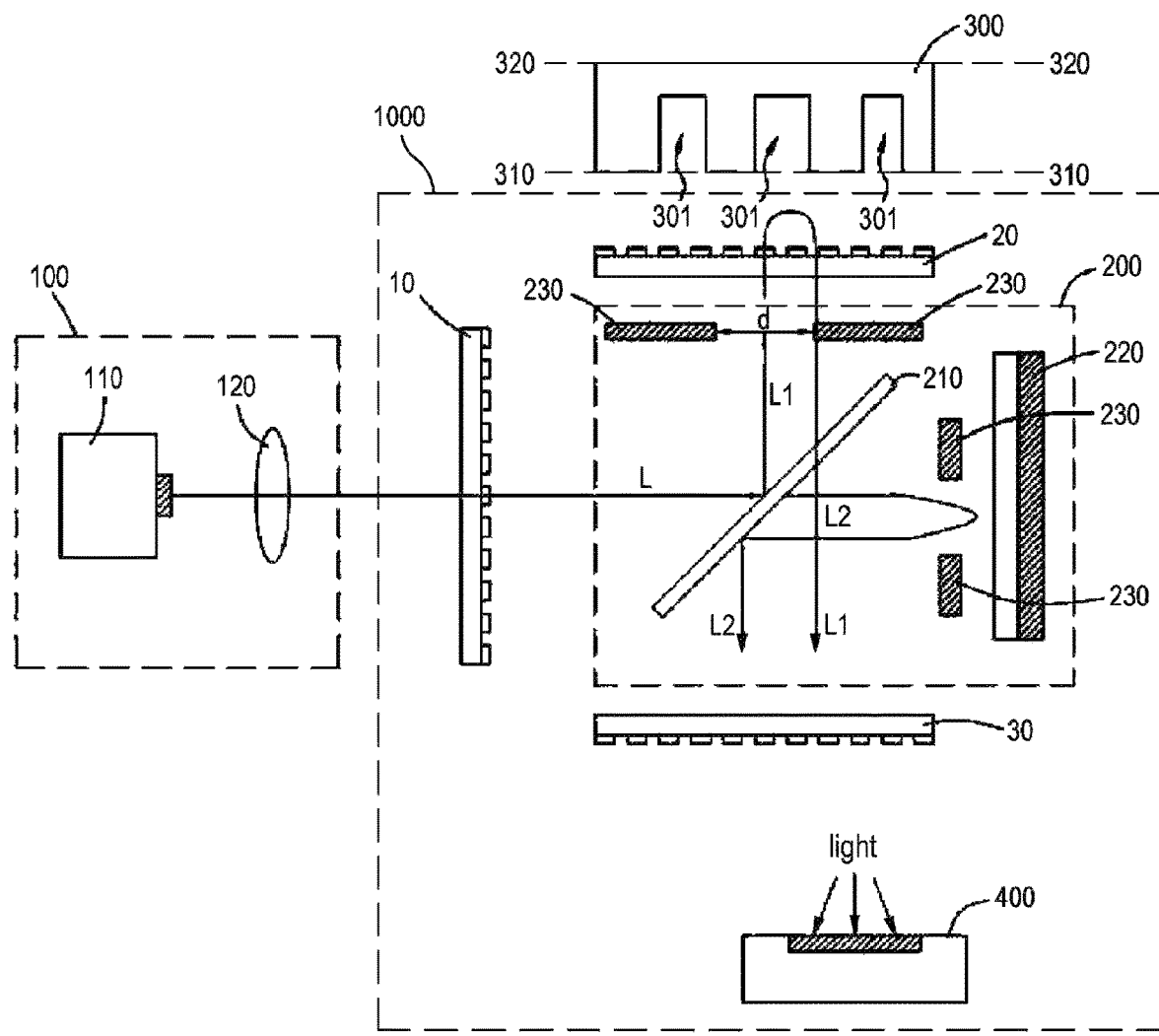
FIG. 1 illustrates a conceptual diagram of a three-dimensional shape measuring apparatus using a diffraction grating according to an embodiment of the present invention.

In the present specification, the terms are merely used to describe a specific embodiment, and are not intended to limit the present invention. Singular forms may include plural forms as well unless the context clearly indicates otherwise. Further, in the present specification, the terms "include," "have," and their conjugates are intended merely to denote the existence of a described feature, numeral, step, operation, element, component, or a combination thereof, and should not be construed to initially exclude the existence of or the possibility of addition of one or more other features, numerals, steps, operations, elements, components, or combinations thereof.

Unless defined differently, all terms used herein, which include technical terminologies or scientific terminologies, have the same meanings as those generally understood by a person skilled in the art to which the present invention belongs. It should be interpreted that the terms, which are identical to those defined in general dictionaries, have the meanings identical to those in the context of the related technique. The terms should not be ideally or excessively interpreted as a formal meaning unless not clearly defined by the present specification. The same reference signs presented in drawings indicate the same members. In describing embodiments, a detailed description of related known configurations or functions will be omitted when it is determined that the detailed description may unnecessarily obscure the subject matter of the present invention. Further, the size of each of elements in the drawings may be exaggerated for the description thereof, and does not mean a size which is actually applied.

In the present specification, even in different embodiments, an identical or similar reference numeral is assigned to an identical or similar element, and the description made initially will be applied thereto. Singular forms used in the present specification may include plural forms as well unless the context clearly indicates otherwise. The suffixes of elements used in the following descriptions, such as "module" and "unit," are assigned or used together only for ease in composing the specification, but they do not have distinguishing meanings or roles.

In describing the present invention, although the terms, such as first, second and the like, may be used to describe various elements, the elements should not be limited by the terms. The terms are used merely for the purpose of distinguishing one element from another element. For example, a first element may be termed a second element, and similarly, a second element may be termed a first element, without departing from the scope of the present invention.

Hereinafter, embodiments of the present invention will be described in detail with reference to the drawings.

FIG. 1 illustrates a conceptual diagram of a three-dimensional shape measuring apparatus using a diffraction grating according to an embodiment of the present invention. Referring to FIG. 1, the three-dimensional shape measuring apparatus 1000 using the diffraction grating according to an embodiment of the present invention may include a frequency scanning interferometer 200, an image sensor unit 400, and at least one diffraction grating 10, 20, or 30. In another embodiment, the three-dimensional shape measurement apparatus 1000 may further include a light source unit 100.

In one embodiment, the light source unit 100 may include a light diode 110 (e.g., laser diode, etc.), and may further include a collimator lens 120. The light diode 110 may output a laser light, and the light output from the light diode 110 is incident on the collimator lens 120. The collimator lens 120 may converge the light, which is output and diverges from the light diode 110, to output a collimated light. As illustrated in FIG. 1, the light output from the light source unit 100 may travel to the frequency scanning interferometer 200 along an optical path L.

In one embodiment, the frequency scanning interferometer 200 may be disposed in front of the light source unit 100 as shown in FIG. 1, and may include a light splitter 210, which is installed in the traveling direction of light generated from the light source unit 100 to reflect a portion of the light along a first path L1 and to transmit a portion of the light along a second path L2.

For example, the light splitter 210 may include a beam splitter (BS) or a polarizing beam splitter (PBS).

A measurement target 300 may be disposed in the traveling direction of the light reflected along the first path L1. The measurement target 300 may include a front surface 310, on which at least one hole 301 is disposed, and a rear surface 320 disposed at the opposite side of the front surface 310. Alternatively, the measurement target 300 may be a substrate including at least one via hole. For example, the measurement target 300 may be a silicon wafer used in semiconductor packaging but is not limited thereto.

The light reflected by the light splitter 210 to travel along the first path L1, such as the optical path L1 illustrated in FIG. 1, may travel to the measurement target 300 to be reflected therefrom, and then travel to the image sensor unit 400.

The image sensor unit 400 may receive the light that travels along the first path L1 and is reflected from the measurement target 300, and measure the shape of the measurement target 300. Specifically, the image sensor unit 400 may generate an image of the measurement target 300 through the received light, and an observer may observe a shape of the measurement target 300 through the image generated as described above. Further, the image sensor unit 400 may include a plurality of image sensors, which receive lights having the different parallax information through a single imaging lens and generate a plurality of images according to the respectively different parallax information. This will be described in more detail below.

When a typical frequency scanning interferometer is used, a light incident on a measurement target includes only a light vertically incident thereon. However, the shape measuring apparatus of the present invention employs a diffraction grating to use lights which are incident on a measurement target from various angles and then reflected by the measurement target. By using such lights incident from various angles and reflected as described above, the depth of a hole of the measurement target and an inner wall of the hole can be simultaneously observed from various angles.

Figure 2:
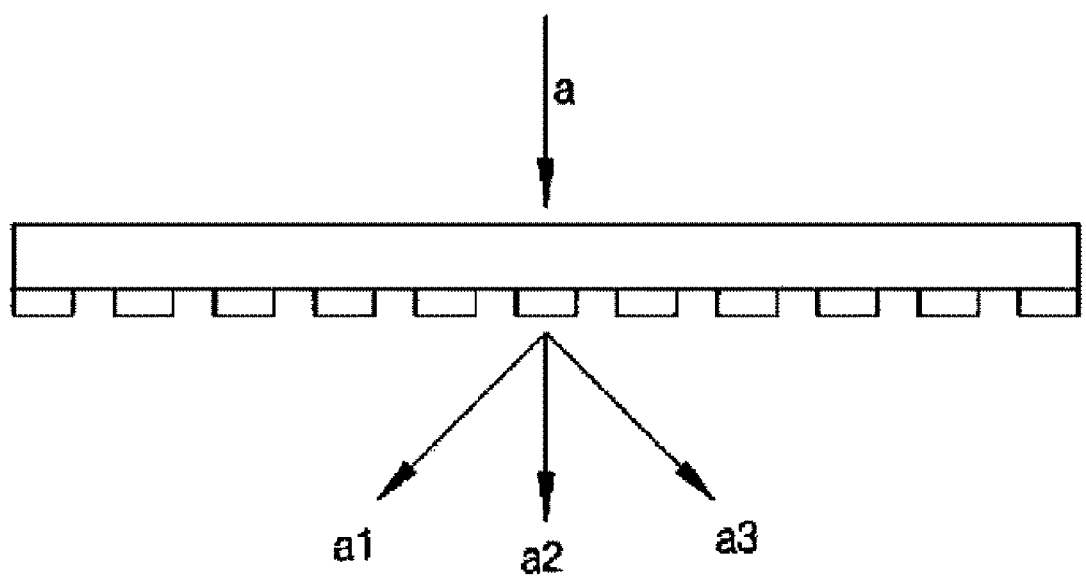
FIG. 2 illustrates a conceptual diagram for describing functions of a diffraction grating of a three-dimensional shape measuring apparatus according to an embodiment of the present invention.

FIG. 2 illustrates a conceptual diagram for describing functions of a diffraction grating of a three-dimensional shape measuring apparatus according to an embodiment of the present invention. In FIG. 2, for the sake of explanation, among the various locations of the diffraction gratings that can be implemented in the present invention, a description will be made of an apparatus having only the diffraction grating 20 among the diffraction gratings 10, 20, and 30 of FIG. 1. Referring to FIG. 2, a light incident on the diffraction grating passes through the diffraction grating and travels along a plurality of paths a1, a2, and a3 having different parallax information. The lights having different parallaxes and traveling as described above may be incident on the measurement target 300 and may then be reflected therefrom.

The three-dimensional shape measuring apparatus 1000 using the diffraction grating according to an embodiment of the present invention may include, as illustrated in FIG. 1, at least one diffraction grating among a diffraction grating 10 disposed on a light path between the light source unit 100 and the light splitter 210, a diffraction grating 20 disposed on a light path between the measurement target 300 and the light splitter 210, and a diffraction grating 30 disposed on a light path between the measurement target 300 and the image sensor unit 400. In other words, at least one of the diffraction gratings 10, 20, and 30 of FIG. 1 may be included in the three-dimensional shape measuring apparatus 1000 according to an embodiment of the present invention.

In the present invention, when the three-dimensional shape measuring apparatus 1000 using a diffraction grating includes the diffraction grating 10 disposed on the light path between the light source unit 100 and the light splitter 210, the light generated by the light source unit 100 may travel at various angles so as to achieve an effect of illumination at various angles.

Further, when the three-dimensional shape measuring apparatus 1000 using a diffraction grating includes the diffraction grating 30 disposed on the light path in front of the image sensor unit 400, the diffraction grating 30 is disposed at the front surface part of the image sensor unit, and thus the apparatus can be easily manufactured. Although the diffraction gratings 10, 20, and 30 are illustrated to have a concavo-convex form in FIG. 1, they are not limited thereto. In other embodiments, the diffraction gratings may have the form of one among a lens array form, a lenticular form, a prism array form, a wire grid form, a concavo-convex form, a right triangle array form, and an isosceles triangle array form.

Figure 3:
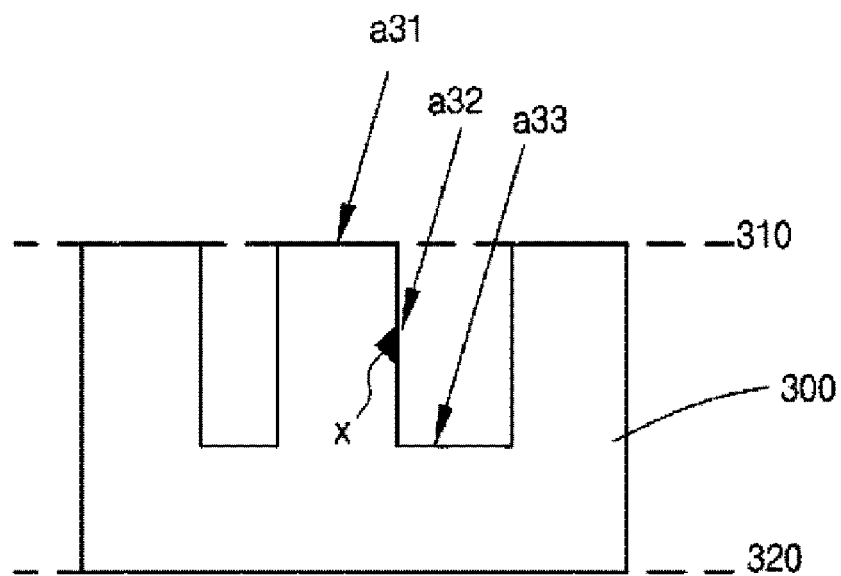
FIG. 3 illustrates a conceptual diagram for describing a form in which lights having different parallax information are incident on a measurement target.

FIG. 3 illustrates a conceptual diagram for describing a form in which lights having different parallax information are incident on a measurement target. Referring to FIG. 3, when diffracted lights a31, a32, and a33 are incident on a hole and an upper part of the measurement target 300 and each of the lights incident on the measurement target 300 has a constant angle as shown in FIG. 3, a light can travel to an inner wall of the hole. The image sensor unit 400 can acquire an image of the inner wall of the hole of the measurement target 300 by using lights incident on the image sensor unit 400. Further, since a plurality of lights having different parallax information may be incident on the image sensor unit 400, the image sensor unit 400 may acquire a plurality of images of the inner wall of the hole which is viewed at various angles.

In FIG. 3, the light a32 is incident on the inner wall of the hole and the image sensor unit 400 may acquire an image of a crack x existing in the inner wall of the hole through the light generated by the reflection of the light a32.

Further, lights received by the image sensor unit 400 include lights having different parallax information such as lights a31, a32, and a33. Thus, the image sensor unit 400 may generate a plurality of images according to the respectively different parallax information. In order to receive such plurality of lights having different parallax information and generate an image as described above, the image sensor unit 400 may include a parallax image array.

Figure 4:
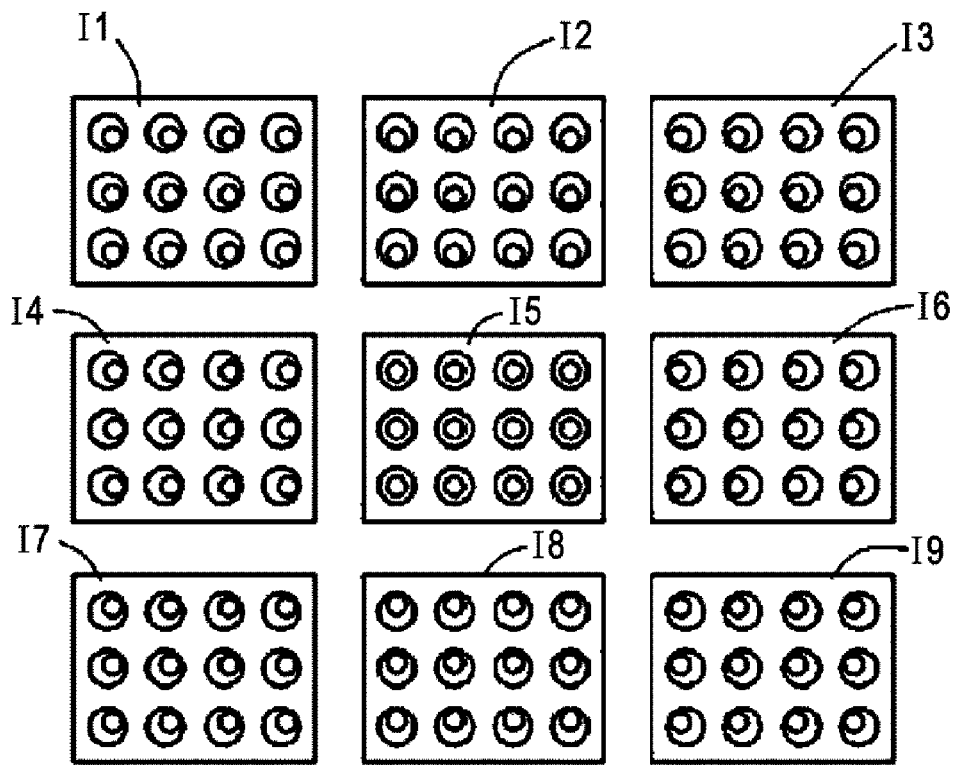
FIG. 4 illustrates nine images having different parallaxes that are generated with respect to a part of a measurement target including 12 holes (4×3).

FIG. 4 illustrates nine image arrays having different parallaxes that are acquired with respect to an identical part of a measurement target, which includes 12 holes (4×3). In the present invention, as shown in FIG. 4, the images generated by the image sensor unit 400 may include a plurality of images having different parallax information due to light diffraction by a diffraction grating. In FIG. 4, it is may be understood that although an inner wall of a hole is not visible in an image I5 acquired through vertically incident light, the shape of the inner wall of the hole can be observed from different viewpoints through other images I1, I2, I3, I4, I6, I7, I8, and I9.

In order to generate an image of the measurement target 300, the image sensor unit 400 may use only the light reflected by the measurement target 300. Alternatively, the image sensor unit 400 may generate an image of the measurement target 300 by using the light reflected by the measurement target 300 together with another light (i.e., a reference light).

Figure 5:
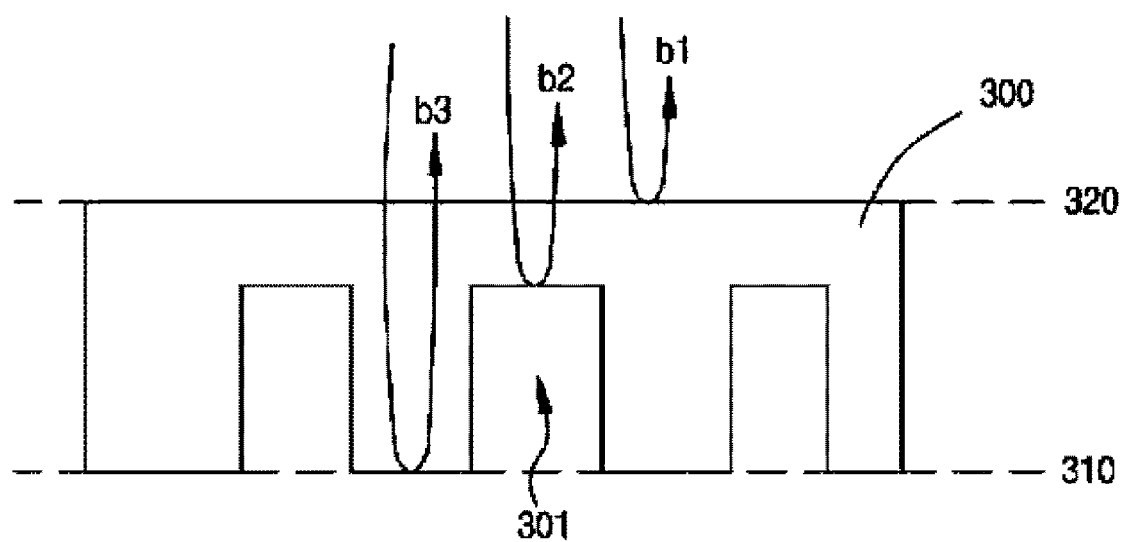
FIG. 5 illustrates a conceptual diagram for describing the case where an image sensor unit uses only a light reflected from a measurement target.

FIG. 5 illustrates a conceptual diagram for describing the case where the image sensor unit 400 uses only a light reflected by the measurement target 300. Referring to FIG. 5, the measurement target 300 may be disposed so that a light incident from the light splitter 210 is incident not on the front surface 310, where a hole of the measurement target 300 is formed, but on the rear surface 320.

A light emitted from the light source unit 100 and reflected by the light splitter 210 has a characteristic of passing through the measurement target 300, and a light incident on the measurement target 300 may be reflected by the front surface 310, the rear surface 320, and the bottom surface of the hole 301. Accordingly, paths of light b1 reflected by the rear surface 320 of the measurement target 300, light b2 reflected by the bottom surface of the hole, and light b3 reflected by the front surface are formed, and each of the reflected lights may be received by the image sensor unit 400. The image sensor unit 400 may measure the depth of the hole of the measurement target 300 by using at least one of the lights b1-b3 interfering with the light reflected by the bottom surface of the hole positioned inward of the rear surface of the measurement target. In other words, the image sensor unit 400 may measure the shape of the measurement target by receiving lights interfered with the light reflected by the bottom surface of the hole positioned inward of the rear surface of the measurement target. In this case, since the image sensor does not use any reference mirror, it is not affected substantially by vibration. Further, the movement speed can be increased and signal stability can be enhanced.

The three-dimensional shape measuring apparatus 1000 using a diffraction grating according to another embodiment may further include a reference mirror 220, which forms a reference light to interfere with the light reflected by the measurement target by disposing the reference mirror 220 in the traveling direction of light transmitted along the second path L2. Referring to FIG. 1 again, a light path of the reference light may be L2 of FIG. 1. When the reference mirror 220 is further included, the image sensor unit 400 may measure the shape of the measurement target 300 by using an interference signal of the reference light and the light reflected by the measurement target 300.

Further, in one embodiment, in order to prevent parallax images from overlapping each other, the frequency scanning interferometer 200 may include a light blocking unit 230 so that the light transmitted through or reflected by the light splitter 210 is incident on the measurement target 300 or on the reference mirror 220 in a constant width. Herein, the width d of an open aperture of the light blocking unit 230, which limits the width of the light incident on the measurement target 300, may be determined by using at least one among a distance between the diffraction grating 20 and the measurement target 300 (e.g., a case where the diffraction grating is disposed between the measurement target and the light splitter), the size of a FOV (field of view) of an observation area of the measurement target 300, and a distance between the light blocking unit 230 and the measurement target 300.

Meanwhile, the field of use of the prior art document, "Applicability of diffraction grating to parallax image array generation in integral imaging," is different from that of the present invention using an interferometer. Further, in the present invention, the diffraction grating 10 disposed between the light splitter and the light source unit and the diffraction grating 30, which receives and diffracts the light reflected by the measurement target and the light reflected by the reference mirror, are one of important features of the present invention, which are not disclosed in the prior art.

The three-dimensional shape measuring apparatus 1000 using a diffraction grating may obtain, in a visual inspection optical system using a laser, multi-view images without distortion to acquire information on a blind spot, which cannot be solved by a conventional inspection system having only a single viewpoint. Further, the apparatus may acquire more precise three-dimensional information by using parallax information.

Further, the three-dimensional shape measuring apparatus 1000 using a diffraction grating is suitable for measuring a very thin and deep via hole (e.g., a through silicon via) that has an opening diameter of several μm to several hundred μm and an aspect ratio (depth to opening diameter of hole) of about 10:1.

Further, by using a diffraction grating, the present invention can obtain a multi-view image through a single camera without an image distortion of a three-dimensional measurement target and a focal problem.

As above, the present invention has been described with reference to embodiments illustrated in drawings. However, the embodiments are merely for illustrative purposes and a person skilled in the art will understand that various modifications thereof and variations therefrom are possible. However, the modifications and variations as described above should be considered to be within the technical protection scope of the present invention. Therefore, the true technical protection scope of the present invention should be defined by a technical spirit of the accompanying claims.

What is claimed is:

1. A three-dimensional shape measuring apparatus using a diffraction grating, comprising:
    a light splitter installed in a traveling direction of a light generated from a light source unit, and configured to reflect a portion of the light along a first path and transmit a portion of the light along a second path;
    an image sensor unit configured to receive a light traveling along the first path and reflected from a measurement target having at least one hole, and measure the shape of the measurement target; and
    a diffraction grating disposed on a light path between the light source unit and the light splitter,
    wherein the diffraction grating diffracts a light incident on the diffraction grating so that lights having passed through the diffraction grating have different parallax information, and
    wherein the image sensor unit receives the lights having the different parallax information and generates a plurality of different images based on the different parallax information.

2. The apparatus of claim 1, wherein the image sensor unit comprises a plurality of image sensors configured to receive the lights having the different parallax information through a single imaging lens and generate the plurality of different images based on the different parallax information.

3. The apparatus of claim 1, wherein the measurement target is disposed to reflect the light reflected along the first path by a front surface on which the hole is formed or a rear surface.

4. The apparatus of claim 3, wherein when the measurement target is disposed to reflect the light reflected along the first path by the rear surface, the image sensor unit measures the shape of the measurement target by receiving the light reflected from the rear surface of the measurement target and a light reflected from a bottom surface of the hole positioned inward of the rear surface of the measurement target that interfere with each other.

5. The apparatus of claim 1, further comprising a reference mirror disposed in a traveling direction of the light transmitted along the second path to form a reference light to interfere with the light reflected from the measurement target, wherein the image sensor unit measures the shape of the measurement target by using an interference signal according to superposition of the light reflected from the measurement target and the reference light.

6. The apparatus of claim 1, wherein the diffraction grating has a form of at least one among a lens array form, a lenticular form, a prism array form, a wire grid form, a concavo-convex form, a right triangle array form, and an isosceles triangle array form.

7. The apparatus of claim 1, wherein the three-dimensional shape measuring apparatus using the diffraction grating measures a three-dimensional shape of a via hole of a substrate as the measurement target.

8. The apparatus of claim 1, wherein the plurality of different images are indicative of the at least one hole which is viewed at a plurality of angles.

* * * * *